(12) United States Patent
Blacker et al.

(10) Patent No.: US 6,509,467 B1
(45) Date of Patent: Jan. 21, 2003

(54) TRANSFER HYDROGENATION PROCESS

(75) Inventors: Andrew John Blacker, Huddersfield (GB); Lynne Alison Campbell, Grangemouth (GB)

(73) Assignee: Avecia Limited, Blackley (GB)

( * ) Notice: Subject to any disclaimer, the term of this patent is extended or adjusted under 35 U.S.C. 154(b) by 0 days.

(21) Appl. No.: 09/787,707

(22) PCT Filed: Sep. 22, 1999

(86) PCT No.: PCT/GB99/03176

§ 371 (c)(1),
(2), (4) Date: Mar. 21, 2001

(87) PCT Pub. No.: WO00/18708

PCT Pub. Date: Apr. 6, 2000

(30) Foreign Application Priority Data

Sep. 29, 1998 (GB) .............................. 9821067

(51) Int. Cl.$^7$ .................. C07B 53/00; C07B 43/04; C07D 217/10; C07D 209/08
(52) U.S. Cl. ............ 546/139; 546/144; 546/148; 546/150; 548/469; 548/490; 564/248; 564/269; 564/271; 564/272; 564/273; 564/274; 564/275; 564/278; 564/279
(58) Field of Search ................. 564/248, 269, 564/271, 272, 273, 274, 275, 278, 279; 546/139, 150, 144, 148; 548/490, 469

(56) References Cited

FOREIGN PATENT DOCUMENTS

| AT | 333 764 | 12/1976 |
| WO | WO 98/42643 | 10/1998 |

OTHER PUBLICATIONS

N. Uematsu: "Asymmetric transfer hydrogenation of imines" Journal of The American Chemical Society, vol. 118, No. 20, May 22, 1996, pp. 4916–4917, XP002069432 DC US, the whole document.

*Primary Examiner*—Brian J. Davis
(74) *Attorney, Agent, or Firm*—Pillsbury Winthrop LLP

(57) ABSTRACT

A catalytic transfer hydrogenation process is provided. The catalyst employed in the process is a metal neutral hydrocarbyl complex which is coordinated to defined bidentate ligands. Preferred metals include rhodium, ruthenium and iridium. Preferred bidentate ligands are diamines and aminoalcohols, particularly those comprising chiral centers. The hydrogen donor is advantageously a mixture of triethylamine and formic acid. The process can be employed to transfer hydrogenate iminium salts, which are preferably prochiral.

20 Claims, No Drawings

TRANSFER HYDROGENATION PROCESS

This application is the national phase of international application PCT/GB99/03176 filed Sep. 22, 1999 which designated the U.S.

This invention relates to catalytic transfer hydrogenation, particularly in the presence of a complexed transition metal, and to a process of making optically active compounds.

According to a first aspect of the present invention there is provided a process for the transfer hydrogenation of a compound of formula (1)

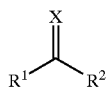

(1)

wherein:

X represents $(NR^3R^4)^+Q^-$, $N^+R^5{-}O^{31}$, $(NR^6OR^7)^+Q^-$, $(NR^8NR^9R^{10})^+Q^{31}$, $(NR^8NR^9C({=}NR^{11})R^{12})^+Q^-$, $(NR^8NR^9SO_2R^{13})^+Q^-$, or $(NR^8NR^9COR^{14})^+Q^-$;

$Q^-$ represents a monovalent anion;

$R^1$, $R^2$, $R^3$, $R^4$, $R^5$, $R^6$, $R^7$, $R^8$, $R^9$, $R^{10}$, and $R^{11}$ each independently represents a hydrogen atom, an optionally substituted hydrocarbyl, a perhalogenated hydrocarbyl or an optionally substituted heterocyclyl group, one or more of $R^1$ & $R^2$, $R^1$ & $R^3$, $R^2$ & $R^4$, $R^3$ & $R^4$, $R^1$ & $R^5$, $R^1$ & $R^6$, $R^2$ & $R^7$, $R^1$ & $R^8$, $R^1$ & $R^9$, $R^6$ & $R^7$, $R^8$ & $R^9$ and $R^9$ & $R^{10}$ optionally being linked in such a way as to form an optionally substituted ring(s); and $R^{12}$, $R^{13}$ and $R^{14}$ each independently represents an optionally substituted hydrocarbyl, a perhalogenated hydrocarbyl or an optionally substituted heterocyclyl group;

said process comprising reacting the compound of formula (1) with a hydrogen donor in the presence of a catalyst, characterised in that the catalyst has the general formula:

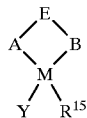

wherein:

$R^{15}$ represents a neutral optionally substituted hydrocarbyl or perhalogenated hydrocarbyl ligand;

A represents $-NR^{16}-$, $-NR^{17}-$, $-NHR^{16}$, $-NR^{16}R^{17}$ or $-NR^{17}R^{18}$ where $R^{16}$ is H, $C(O)R^{18}$, $SO_2R^{18}$, $C(O)NR^{18}R^{22}$, $C(S)NR^{18}R^{22}$, $C({=}NR^{22})SR^{23}$ or $C({=}NR^{22})OR^{23}$, $R^{17}$ and $R^{18}$ each independently represents an optionally substituted hydrocarbyl, perhalogenated hydrocarbyl or an optionally substituted heterocyclyl group, and $R^{22}$ and $R^{23}$ are each independently hydrogen or a group as defined for $R^{18}$;

B represents $-O-$, $-OH$, $OR^{19}$, $-S-$, $-SH$, $SR^{19}$, $-NR^{19}-$, $-NR^{20}-$, $-NHR^{20}$, $-NR^{19}R^{20}$, $-NR^{19}R^{21}$, $-PR^{19}-$ or $-PR^{19}R^{21}$ where $R^{20}$ is H, $C(O)R^{21}$, $SO_2R^{21}$, $C(O)NR^{21}R^{24}$, $C(S)NR^{21}R^{24}$, $C({=}NR^{24})SR^{25}$ or $C({=}NR^{24})OR^{25}$, $R^{19}$ and $R^{21}$ each independently represents an optionally substituted hydrocarbyl, perhalogenated hydrocarbyl or an optionally substituted heterocyclyl group, and $R^{24}$ and $R^{25}$ are each independently hydrogen or a group as defined for $R^{21}$;

E represents a linking group;

M represents a metal capable of catalysing transfer hydrogenation; and

Y represents an anionic group, a basic ligand or a vacant site;

provided that when Y is not a vacant site that at least one of A or B carries a hydrogen atom.

The catalytic species is believed to be substantially as represented in the above formula. It may be introduced on a solid support.

When X represents $(NR^3R^4)^+Q^{31}$, compounds of formula (1) are iminium salts. Iminium salts include protonated imine salts and quaternary imine salts, preferably quaternary imine salts. Quaternary imine salts are represented by compounds of formula (1) in which both $R^3$ and $R^4$ are not hydrogen.

Anions which may be represented by $Q^-$ include halides, optionally substituted arylsulphonates, such as optionally substituted phenyl and napthyl sulphonates, optionally substituted alkylsulphonates including halogenated alkylsulphonates, such as $C_{1-20}$alkylsulphonates, optionally substituted carboxylates, such as $C_{1-10}$ alkyl and aryl carboxylates, ions derived from the polyhalogenation of boron, phosphorous or antimony, and other common inorganic ions for example perchlorate. Examples of anions which may be present are bromide, chloride, iodide, hydrogen sulphate, tosylate, formate, acetate, tetrafluoroborate, hexafluorophosphate, hexafluoroantimonate, perchlorate, trifluoromethanesulphonate and trifluoroacetate. Preferred anions include bromide, chloride, iodide, formate and trifluoroacetate, particularly preferred anions include iodide, formate and trifluoroacetate.

Hydrocarbyl groups which may be represented by $R^{1-14}$, $R^{17}$, $R^{18}$, $R^{19}$ and $R^{21-25}$ independently include alkyl, alkenyl and aryl groups, and any combination thereof, such as aralkyl and alkaryl, for example benzyl groups.

Alkyl groups which may be represented by $R^{1-14}$, $R^{17}$, $R^{18}$, $R^{19}$ and $R^{21-25}$ include linear and branched alkyl groups comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, commonly comprising from 3 to 10 carbon atoms in the largest ring and optionally featuring one or more bridging rings. Examples of alkyl groups which may be represented by $R^{1-14}$, $R^{17}$, $R^{18}$, $R^{19}$ and $R^{21-25}$ include methyl, ethyl, propyl, 2-propyl, butyl, 2-butyl, t-butyl and cyclohexyl groups.

Alkenyl groups which may be represented by $R^{1-14}$, $R^{17}$, $R^{18}$, $R^{19}$ and $R^{21-25}$ include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups. When either of $R^1$ or $R^2$ represents an alkenyl group, a carbon-carbon double bond is preferably located at the position β to the C=X moiety. When either of $R^1$ or $R^2$ represents an alkenyl group, the compound of formula (1) is preferably an α,β-unsaturated iminium compound.

Aryl groups which may be represented by $R^{1-14}$, $R^{17}$, $R^{18}$, $R^{19}$ and $R^{21-25}$ may contain 1 ring or 2 or more fused rings which may include cycloalkyl, aryl or heterocyclic rings. Examples of aryl groups which may be represented by $R^{1-14}$, $R^{17}$, $R^{18}$, $R^{19}$ and $R^{21-25}$ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by $R^{1-14}$, $R^{17}$, $R^{18}$, $R^{19}$ and $R^{21-25}$ independently include perhalogenated alkyl and aryl groups, and any combination thereof, such as aralkyl and alkaryl groups. Examples of perhalogenated alkyl groups which may be represented by $R^{1-14}$, $R^{17}$, $R^{18}$, $R^{19}$ and $R^{21-25}$ include —$CF_3$ and —$C_2F_5$.

Heterocyclic groups which may be represented by $R^{1-14}$, $R^{17}$, $R^{18}$, $R^{19}$ and $R^{21-25}$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. When either of $R^1$ or $R^2$ represents or comprises a heterocyclic group, the atom in $R^1$ or $R^2$ bonded to the C=X group is preferably a carbon atom. Examples of heterocyclic groups which may be represented by $R^{1-14}$, $R^{17}$, $R^{18}$, $R^{19}$ and $R^{21-25}$ include pyridyl, pyrimidyl, pyrrolyl, thiophenyl, furanyl, indolyl, quinolyl, isoquinolyl, imidazoyl and triazoyl groups.

When any of $R^{1-14}$, $R^{17}$, $R^{18}$, $R^{19}$ and $R^{21-25}$ is a substituted hydrocarbyl or heterocyclic group, the substituent(s) should be such so as not to adversely affect the rate or stereoselectivety of the reaction. Optional substituents include halogen, cyano, nitro, hydroxy, amino, thiol, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for $R^1$ above. One or more substituents may be present.

When any of $R^1$ & $R^2$, $R^1$ & $R^3$, $R^2$ & $R^4$, $R^3$ & $R^4$, $R^1$ & $R^5$, $R^1$ & $R^6$, $R^2$ & $R^7$, $R^1$ & $R^8$, $R^1$ & $R^9$, $R^6$ & $R^7$, $R^8$ & $R^9$ and $R^9$ & $R^{10}$ are linked in such a way that when taken together with either the carbon atom and/or atom X of the compound of formula (1) that a ring is formed, it is preferred that these be 5, 6 or 7 membered rings. The rings formed in this way may additionally be fused to each other or to other ring systems. Examples of rings which may be so formed include

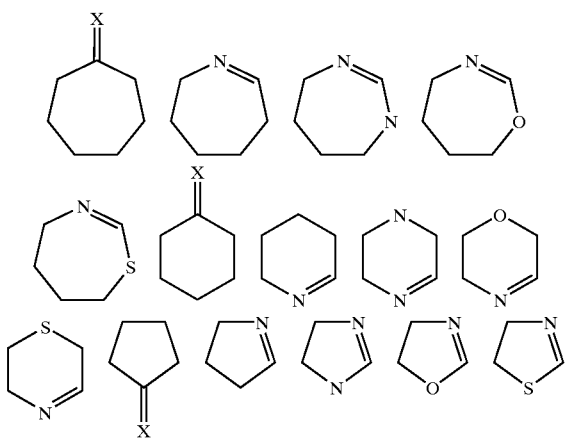

wherein X is as defined above and the rings may be optionally substituted or may be fused to other rings.

In certain preferred embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are all independently $C_{1-6}$ alkyl or are a combination of aryl, particularly phenyl, $C_{1-6}$ alkyl and $C_{6-10}$ aralkyl. Substituents may be present, particularly substituents para to the C=X group when one or more of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a phenyl group.

In especially preferred embodiments, $R^4$, $R^5$, $R^6$, or $R^8$ are $C_{1-6}$ alkyl or $C_{6-10}$ aralkyl, especially methyl, benzyl or $PhCHCH_3$.

In certain highly preferred embodiments, X is a group of formula $(NR^3R^4)^+Q^-$ and $R^1$ and $R^3$ are linked in such a way that when taken together with the carbon atom and the nitrogen atom of the C=X group of the compound of formula (1) that a 5, 6 or 7 membered ring is formed, $R^4$ is $C_{1-6}$ alkyl or $C_{6-10}$ aralkyl, especially methyl, benzyl or $PhCHCH_3$, and $R^2$ is optionally substituted hydrocarbyl, preferably $C_{1-6}$ alkyl, or optionally substituted phenyl especially methoxy, hydroxy or fluoro substituted phenyl. The 5, 6 or 7 membered ring formed by linking $R^1$ and $R^3$ optionally may be fused to another ring system, preferably a benzenoid system which may be substituted, preferred substituents include hydroxy, methoxy and fluoro.

Most advantageously, the compound of formula (1) is prochiral, such that the hydrogenated product comprises a chiral atom to which $R^1$, $R^2$ and X are each bonded. Such an asymmetric transfer hydrogenation process forms an especially preferred aspect of the present invention. Most commonly, when the compound of formula (1) is prochiral, $R^1$ and $R^2$ are different, and neither is hydrogen. Advantageously, one of $R^1$ and $R^2$ is aliphatic and the other is aryl or heterocyclyl.

Examples of compounds of formula (1) include

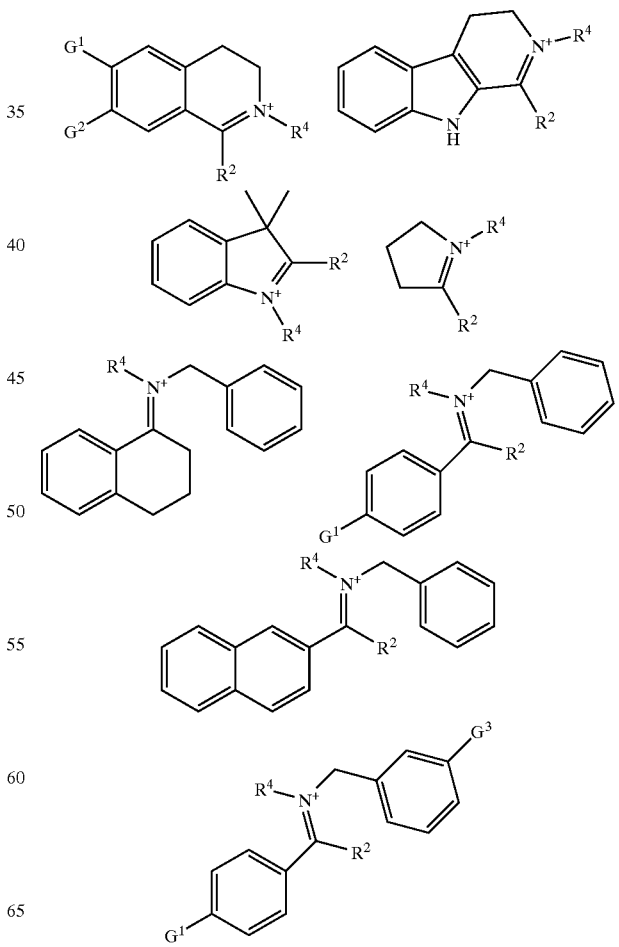

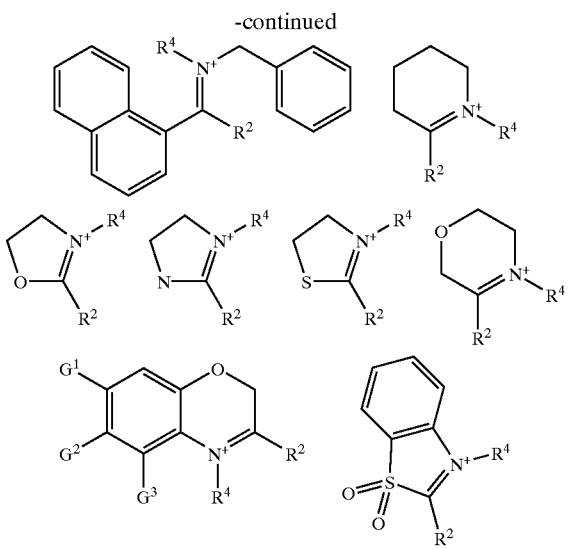

wherein $R^2$ and $R^4$ are as described above and $G^1$, $G^2$ and $G^3$ are independently hydrogen, chloro, bromo, fluoro, iodo, cyano, nitro, hydroxy, amino, thiol, acyl, hydrocarbyl, perhalogentated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for $R^1$ above.

Hydrogen donors include hydrogen, primary and secondary alcohols, primary and secondary amines, carboxylic acids and their esters and amine salts, readily dehydrogenatable hydrocarbons, clean reducing agents, and any combination thereof.

Primary and secondary alcohols which may be employed as hydrogen donors comprise commonly from 1 to 10 carbon atoms, preferably from 2 to 7 carbon atoms, and more preferably 3 or 4 carbon atoms. Examples of primary and secondary alcohols which may be represented as hydrogen donors include methanol, ethanol, propan-1-ol, propan-2-ol, butan-1-ol, butan-2-ol, cyclopentanol, cyclohexanol, benzylalcohol, and menthol. When the hydrogen donor is an alcohol, secondary alcohols are preferred, especially propan-2-ol and butan-2-ol.

Primary and secondary amines which may be employed as hydrogen donors comprise commonly from 1 to 20 carbon atoms, preferably from 2 to 14 carbon atoms, and more preferably 3 or 8 carbon atoms. Examples of primary and secondary amines which may be represented as hydrogen donors include ethylamine, propylamine, isopropylamine, butylamine, isobutylamine, hexylamine, diethylamine, dipropylamine, di-isopropylamine, dibutylamine, di-isobutylamine, dihexylamine, benzylamine, dibenzylamine and piperidine. When the hydrogen donor is an amine, primary amines are preferred, especially primary amines comprising a secondary alkyl group, particularly isopropylamine and isobutylamine.

Carboxylic acids or their esters which may be employed as hydrogen donors comprise commonly from 1 to 10 carbon atoms, preferably from 1 to 3 carbon atoms. In certain embodiments, the carboxylic acid is advantageously a beta-hydroxy-carboxylic acid. Esters may be derived from the carboxylic acid and a $C_{1-10}$ alcohol. Examples of carboxylic acids which may be employed as hydrogen donors include formic acid, lactic acid, ascorbic acid and mandelic acid. The most preferred carboxylic acid is formic acid. In certain preferred embodiments, when a carboxylic acid is employed as hydrogen donor, at least some of the carboxylic acid is preferably present as salt, preferably an amine, ammonium or metal salt. Preferably, when a metal salt is present the metal is selected from the alkali or alkaline earth metals of the periodic table, and more preferably is selected from the group I elements, such as lithium, sodium or potassium. Amines which may be used to form such salts include both aromatic and non-aromatic amines, also primary, secondary and tertiary amines and comprise typically from 1 to 20 carbon atoms. Tertiary amines, especially trialkylamines, are preferred. Examples of amines which may be used to form salts include trimethylamine, triethylamine, di-isopropylethylamine and pyridine. The most preferred amine is triethylamine. When at least some of the carboxylic acid is present as an amine salt, particularly when a mixture of formic acid and triethylamine is employed, the mole ratio of acid to amine is between 1:1 and 50:1 and preferably between 1:1 and 10:1, and most preferably about 5:2. When at least some of the carboxylic acid is present as a metal salt, particularly when a mixture of formic acid and a group I metal salt is employed, the mole ratio of acid to metal ions present is between 1:1 and 50:1 and preferably between 1:1 and 10:1, and most preferably about 2:1. The ratios of acid to salts may be maintained during the course of the reaction by the addition of either component, but usually by the addition of the carboxylic acid.

Readily dehydrogenatable hydrocarbons which may be employed as hydrogen donors comprise hydrocarbons which have a propensity to aromatise or hydrocarbons which have a propensity to form highly conjugated systems. Examples of readily dehydrogenatable hydrocarbons which may be employed by as hydrogen donors include cyclohexadiene, cyclohexene, tetralin, dihydrofuran and terpenes.

Clean reducing agents which may be represented as hydrogen donors comprise reducing agents with a high reduction potential, particularly those having a reduction potential relative to the standard hydrogen electrode of greater than about −0.1 eV, often greater than about −0.5 eV, and preferably greater than about −1 eV. Examples of clean reducing agents which may be represented as hydrogen donors include hydrazine and hydroxylamine.

The most preferred hydrogen donors are propan-2-ol, butan-2-ol, triethylammonium formate and a mixture of triethylammonium formate and formic acid. However, in certain embodiments when the compound of Formula (1) is a protonated imminium salt, it may be desirable to employ a hydrogen donor which is not a carboxylic acid or a salt thereof.

The neutral optionally substituted hydrocarbyl or perhalogenated hydrocarbyl ligand which may be represented by $R^{15}$ includes optionally substituted aryl and alkenyl ligands.

Optionally substituted aryl ligands which may be represented by $R^{15}$ may contain 1 ring or 2 or more fused rings which include cycloalkyl, aryl or heterocyclic rings. Preferably, the ligand comprises a 6 membered aromatic ring. The ring or rings of the aryl ligand are often substituted with hydrocarbyl groups. The substitution pattern and the number of substituents will vary and may be influenced by the number of rings present, but often from 1 to 6 hydrocarbyl substituent groups are present, preferably 2, 3 or 6 hydrocarbyl groups and more preferably 6 hydrocarbyl groups. Preferred hydrocarbyl substituents include methyl, ethyl, iso-propyl, menthyl, neomenthyl and phenyl. Particularly when the aryl ligand is a single ring, the ligand is preferably benzene or a substituted benzene. When the ligand is a perhalogenated hydrocarbyl, preferably it is a polyhalogenated benzene such as hexachlorobenzene or hexafluorobenzne. When the hydrocarbyl substitutents contain enantiomeric and/or diastereomeric centres, it is preferred that the enantiomerically and/or diastereomerically purified forms of these are used. Benzene, p-cymyl, mesitylene and hexamethylbenzene are especially preferred ligands.

Optionally substituted alkenyl ligands which may be represented by $R^{15}$ include $C_{2-30}$, and preferably $C_{6-12}$, alkenes or cycloalkenes with preferably two or more carbon-carbon double bonds, preferably only two carbon-carbon double bonds. The carbon-carbon double bonds may optionally be conjugated to other unsaturated systems which may be present, but are preferably conjugated to each other. The alkenes or cycloalkenes may be substituted preferably with hydrocarbyl substituents. When the alkene has only one double bond, the optionally substituted alkenyl ligand may comprise two separate alkenes. Preferred hydrocarbyl substituents include methyl, ethyl, iso-propyl and phenyl. Examples of optionally substituted alkenyl ligands include cyclo-octa-1,5-diene and 2,5-norbornadiene. Cyclo-octa-1,5-diene is especially preferred.

When either A or B is an amide group represented by —$NR^{16}$—, —$NHR^{16}$, $NR^{16}R^{17}$, —$NR^{20}$—, —$NHR^{20}$ or $NR^{19}R^{20}$ wherein $R^{17}$ and $R^{19}$ are as hereinbefore defined, and where $R^{16}$ or $R^{20}$ is an acyl group represented by —$C(O)R^{18}$ or —$C(O)R^{21}$, $R^{18}$ and $R^{21}$ independently are often linear or branched $C_{1-7}$alkyl, $C_{1-8}$-cycloalkyl or aryl, for example phenyl. Examples of acyl groups which may be represented by $R^{16}$ or $R^{20}$ include benzoyl, acetyl and halogenoacetyl, especially trifluoroacetyl, groups.

When either A or B is present as a sulphonamide group represented by —$NR^{16}$—, —$NHR^{16}$, $NR^{16}R^{17}$, —$NR^{20}$—, —$NHR^{20}$ or $NR^{19}R^{20}$ wherein $R^{17}$ and $R^{19}$ are as hereinbefore defined, and where $R^{16}$ or $R^{20}$ is a sulphonyl group represented by —$S(O)_2R^{18}$ or —$S(O)_2R^{21}$, $R^{18}$ and $R^{21}$ independently are often linear or branched $C_{1-8}$alkyl, $C_{1-8}$cycloalkyl or aryl, for example phenyl. Preferred sulphonyl groups include methanesulphonyl, trifluoromethanesulphonyl and especially p-toluenesulphonyl groups and naphthylsulphonyl groups.

When either of A or B is present as a group represented by —$NR^{16}$—, —$NHR^{16}$, $NR^{16}R^{17}$, —$NR^{20}$—, —$NHR^{20}$ or $NR^{19}R^{20}$ wherein $R^{17}$ and $R^{19}$ are as hereinbefore defined, and where $R^{16}$ or $R^{20}$ is a group represented by $C(O)NR^{18}R^{22}$, $C(S)NR^{18}R^{22}$, $C(=NR^{22})SR^{23}$, $C(=NR^{22})OR^{23}$, $C(O)NR^{21}R^{24}$, $C(S)NR^{21}R^{24}$, $C(=NR^{24})SR^{25}$ or $C(=NR^{24})OR^{25}$, $R^{18}$ and $R^{21}$ independently are often linear or branched $C_{1-8}$alkyl, such as methyl, ethyl, isopropyl, $C_{1-8}$cycloalkyl or aryl, for example phenyl, groups and $R^{22-25}$ are often each independently hydrogen or linear or branched $C_{1-8}$alkyl, such as methyl, ethyl, isopropyl, $C_{1-8}$cycloalkyl or aryl, for example phenyl, groups.

When B is present as a group represented by —$OR^{19}$, —$SR^{19}$, —$PR^{19}$— or —$PR^{19}R^{21}$, $R^{19}$ and $R^{21}$ independently are often linear or branched $C_{1-8}$alkyl, such as methyl, ethyl, isopropyl, $C_{1-8}$cycloalkyl or aryl, for example phenyl.

It will be recognised that the precise nature of A and B will be determined by whether A and/or B are formally bonded to the metal or are coordinated to the metal via a lone pair of electrons.

The groups A and B are connected by a linking group E. The linking group E achieves a suitable conformation of A and B so as to allow both A and B to bond or coordinate to the metal, M. A and B are commonly linked through 2, 3 or 4 atoms. The atoms in E linking A and B may carry one or more substituents. The atoms in E, especially the atoms alpha to A or B, may be linked to A and B, in such a way as to form a heterocyclic ring, preferably a saturated ring, and particularly a 5, 6 or 7-membered ring. Such a ring may be fused to one or more other rings. Often the atoms linking A and B will be carbon atoms. Preferably, one or more of the carbon atoms linking A and B will carry substituents in addition to A or B. Substituent groups include those which may substitute $R^1$, as defined above. Advantageously, any such substituent groups are selected to be groups which do not coordinate with the metal, M. Preferred substituents include halogen, cyano, nitro, sulphonyl, hydrocarbyl, perhalogenated hydrocarbyl and heterocyclyl groups as defined above. Most preferred substituents are $C_{1-6}$ alkyl groups, and phenyl groups. Most preferably, A and B are linked by two carbon atoms, and especially an optionally substituted ethyl moiety. When A and B are linked by two carbon atoms, the two carbon atoms linking A and B may comprise part of an aromatic or aliphatic cyclic group, particularly a 5, 6 or 7-membered ring. Such a ring may be fused to one or more other such rings. Particularly preferred are embodiments in which E represents a 2 carbon atom separation and one or both of the carbon atoms carries an optionally substituted aryl group as defined above or E represents a 2 carbon atom separation which comprises a cyclopentane or cyclohexane ring, optionally fused to a phenyl ring.

E preferably comprises part of a compound having at least one stereospecific centre. Where any or all of the 2, 3 or 4 atoms linking A and B are substituted so as to define at least one stereospecific centre on one or more of these atoms, it is preferred that at least one of the stereospecific centres be located at the atom adjacent to either group A or B. When at least one such stereospecific centre is present, it is advantageously present in an enantiomerically purified state.

When B represents —O— or —OH, and the adjacent atom in E is carbon, it is preferred that B does not form part of a carboxylic group.

Compounds which may be represented by A-E-B, or from which A-E-B may be derived by deprotonation, are often aminoalcohols, including 4-aminoalkan-1-ols, 1-aminoalkan4-ols, 3-aminoalkan-1-ols, 1-aminoalkan-3-ols, and especially 2-aminoalkan-1-ols, 1-aminoalkan-2-ols, 3-aminoalkan-2-ols and 2-aminoalkan-3-ols, and particularly 2-aminoethanols or 3-aminopropanols, or are diamines, including 1,4-diaminoalkanes, 1,3-diaminoalkanes, especially 1,2- or 2,3-diaminoalkanes and particularly ethylenediamines. Further aminoalcohols that may be represented by A-E-B are 2-aminocyclopentanols and 2-aminocyclohexanols, preferably fused to a phenyl ring. Further diamines that may be represented by A-E-B are 1,2-diaminocyclopentanes and 1,2-diaminocyclohexanes, preferably fused to a phenyl ring. The amino groups may advantageously be N-tosylated. When a diamine is represented by A-E-B, preferably at least one amino group is N-tosylated. The aminoalcohols or diamines are advantageously substituted, especially on the linking group, E, by at least one alkyl group, such as a $C_{1-4}$-alkyl, and particularly a methyl, group or at least one aryl group, particularly a phenyl group.

Specific examples of compounds which can be represented by A-E-B and the protonated equivalents from which they may be derived are:

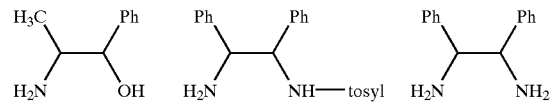

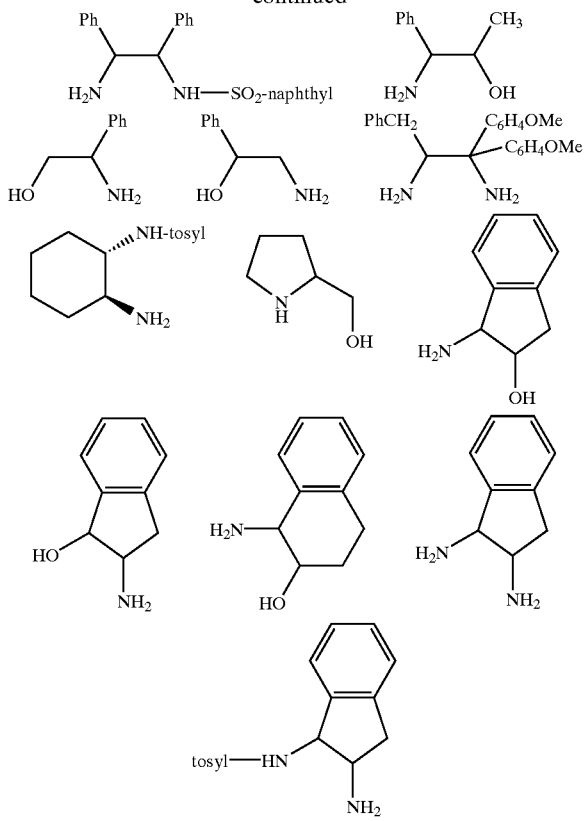

Preferably, the enantiomerically and/or diastereomerically purified forms of these are used. Examples include (1S,2R)-(+)-norephedrine, (1R,2S)-(+)-cis-1-amino-2-indanol, (1S,2R)-2-amino-1,2-diphenylethanol, (1S,2R)-(−)-cis-1-amino-2-indanol, (1R,2S)-(−)-norephedrine, (S)-(+)-2-amino-1-phenylethanol, (1R,2S)-2-amino-1,2-diphenylethanol, N-tosyl-(1R,2R)-1,2-diphenylethylenediamine, N-tosyl-(1S,2S)-1,2-diphenylethylenediamine, (1R,2S)-cis-1,2-indandiamine, (1S,2R)-cis-1,2-indandiamine, (R)-(−)-2-pyrrolidinemethanol and (S)-(+)-2-pyrrolidinemethanol.

Metals which may be represented by M include metals which are capable of catalysing transfer hydrogenation. Preferred metals include transition metals, more preferably the metals in Group VIII of the Periodic Table, especially ruthenium, rhodium or iridium. When the metal is ruthenium it is preferably present in valence state II. When the metal is rhodium or iridium it is preferably present in valence state I.

Anionic groups which may be represented by Y include hydride, hydroxy, hydrocarbyloxy, hydrocarbylamino and halogen groups. Preferably when a halogen is represented by Y, the halogen is chloride. When a hydrocarbyloxy or hydrocarbylamino group is represented by Y, the group may be derived from the deprotonation of the hydrogen donor utilised in the reaction.

Basic ligands which may be represented by Y include water, $C_{1-4}$ alcohols, $C_{1-8}$ primary or secondary amines, or the hydrogen donor which is present in the reaction system. A preferred basic ligand represented by Y is water.

Most preferably, the nature of A-E-B, $R^{15}$ and Y are chosen such that the catalyst is chiral. When such is the case, an enantiomerically and/or diastereomerically purified form is preferably employed. Such catalysts are most advantageously employed in asymmetric transfer hydrogenation processes. In many embodiments, the chirality of the catalyst is derived from the nature of A-E-B.

The process is carried out preferably in the presence of a base, especially when Y is not a vacant site. The $pK_a$ of the base is preferably at least 8.0, especially at least 10.0. Convenient bases are the hydroxides, alkoxides and carbonates of alkali metals; tertiary amines and quaternary ammonium compounds. Preferred bases are sodium 2-propoxide and triethylamine. When the hydrogen donor is not an acid, the quantity of base used can be up to 5.0, commonly up to 3.0, often up to 2.5 and especially in the range 1.0 to 3.5, by moles of the catalyst. When the hydrogen donor is an acid, the catalyst may be contacted with a base prior to the introduction of the hydrogen donor. In such a case, the mole ratio of base to catalyst prior to the introduction of the hydrogen donor is often from 1:1 to 3:1, and preferably about 1:1.

Although gaseous hydrogen may be present, the process is normally operated in the absence of gaseous hydrogen since it appears to be unnecessary.

Advantageously, the process is carried out in the substantial absence of carbon dioxide.

When the product(s) from dehydrogenation of the hydrogen donor is volatile, for example boils at under 100° C., the removal of this volatile product is preferred. The removal can be accomplished by distillation preferably at less than atmospheric pressure or by use of inert gas sparging. When reduced pressure distillation is employed, the pressure is often no more than 500 mmHg, commonly no more than 200 mmHg, preferably in the range of from 5 to 100 mmHg, and most preferably from 10 to 80 mmHg. When the product(s) from dehydrogenation of the hydrogen donor is a gaseous material, for example when formic acid is present as a hydrogen donor, the removal is most preferably accomplished by the use of inert gas sparging, with for example nitrogen.

Suitably the process is carried out at temperatures in the range of from minus 78 to plus 150° C., preferably from minus 20 to plus 110° C. and more preferably from minus 5 to plus 60° C. The initial concentration of the substrate, a compound of formula (1), is suitably in the range 0.05 to 1.0 and, for convenient larger scale operation, can be for example up to 6.0 more especially 0.25 to 2.0, on a molar basis. The molar ratio of the substrate to catalyst is suitably no less than 50:1 and can be up to 50000:1, preferably between 100:1 and 5000:1 and more preferably between 200:1 and 2000:1. The hydrogen donor is preferably employed in a molar excess over the substrate, especially from 5 to 20 fold or, if convenience permits, greater, for example up to 500 fold. After reaction, the mixture is worked up by standard procedures.

During the reaction a solvent may be present, preferably a polar solvent, more preferably a polar aprotic solvent, for example acetonitrile, dimethylformamide or dichloromethane. Conveniently, the hydrogen donor may be the solvent when the hydrogen donor is liquid at the reaction temperature, or it may be used in combination with a diluent. Usually it is preferred to operate in substantial absence of water, but water does not appear to inhibit the reaction. If the hydrogen donor or the reaction solvent is not miscible with water and the desired product is water soluble, it may be desirable to have water present as a second phase extracting the product, pushing the equilibrium and preventing loss of product optical purity as the reaction proceeds. The concentration of substrate may be chosen to optimise reaction time, yield and enantiomeric excess.

The catalytic species is believed to be substantially as represented in the above formula. It may be employed as an oligomer or metathesis product, on a solid support or may be generated in situ.

In certain embodiments it has been found that certain catalysts are preferred for the transfer hydrogenation of iminium salts. Catalysts in which A-E-B is derived from N-tosyldiamines, preferably mono-N-tosyldiamines, particularly mono-N-tosylated ethylenediamines, are preferred. Especially, M is also ruthenium (II) and $R^{15}$ represents an aryl group, or M is iridium (I) or rhodium (I) and $R^{15}$ is cyclo-octadiene. Further, triethylamine is preferably employed as a base, a mixture of formic acid and triethylamine in the preferred ratio of 5:2 (formic acid:triethylamine) is preferably employed as hydrogen donor, and the iminium salt is preferably a protonated imine, or is a methylated or benzylated imine with an iodide, formate or trifluoroacetate counter ion. It is believed that when Y is not a vacant site and when M is rhodium or iridium and is in valence state (I), A-E-B attaches to M by means of two dative bonds (the lone pairs of the heteroatoms in both A and B coordinate to M), whereas when M is ruthenium and is in valence state (II), A-E-B attaches to M by means of one dative and one formal bond.

The catalyst can be made by reacting a metal aryl or alkenyl halide complex with a compound of formula A-E-B as defined above or a protonated equivalent from which it may be derived, and, where Y represents a vacant site, reacting the product thereof with a base. The metal aryl or alkenyl halide complex preferably has the formula $[MR^{15}Z_2]_2$ when M is ruthenium (II) and has the formula $[MR^{15}Z]_2$ when M is iridium or rhodium (I), wherein $R^{15}$ is as defined above, and Z represents a halide, particularly chloride.

For the preparation of the catalysts according to the present invention, a solvent is preferably present. Suitable reaction temperatures are in the range 0–100° C., for example 20–70° C., often giving reaction times of 0.5–24.0 h. After reaction is complete, the catalyst may if desired be isolated, but is more conveniently stored as the solution or used soon after preparation. The solution can contain the hydrogen donor and this, if a secondary alcohol, may be present in or used as the solvent for steps (a) and/or (b). The preparation and after-handling should preferably be under an inert atmosphere, and particularly in carbon dioxide and oxygen-free conditions.

The catalyst or catalyst solution is generally treated with base either just prior to use in a transfer hydrogenation reaction, or during use. This can be accomplished by adding base to the catalyst in solution, or to the compound of formula (1) in solution, or by addition to the transfer hydrogenation reaction.

Iminium salts can generally be obtained by known literature methods, for example the quaternisation of imines, such as by treatment of imines with alkylating agents.

Transfer hydrogenation can be accomplished by transferring the solution of catalyst to a solution of substrate, a compound of general formula I. Alternatively a solution of substrate can be added to a solution of catalyst. Base may be pre-added to the catalyst solution and/or the substrate solution, or can be added later. The hydrogen donor if not already present in the catalyst solution may be added to the substrate solution, or may be added to the reaction mixture.

The invention is illustrated by the following Examples.

EXAMPLE 1

Reduction of N-methyl-1-phenyl-6,7-dimethoxy-3,4-dihydroisoquinolinium iodide

| Catalyst Preparation Reactant | Wt/Vol | Mol.Wt | Mol | Mol ratio |
|---|---|---|---|---|
| [Ru(p-Cymyl)Cl$_2$]$_2$** | 7.6 mg | 612 | 12.4 μmol | 1 |
| (R,R)-N-Tosyl-1,2-diamino-1,2-diphenylethane | 9.1 mg | 366 | 24.9 μmol | 2 |
| Acetonitrile | 10 ml | | | |
| Propan-2-ol | 10 ml | | | |

Notes: **purchased from The Aldrich Chemical Co.

Prior to the reaction, all solvents were degassed, for example: 100 ml of anhydrous propan-2-ol was added by syringe to a sealed clean dry round bottomed flask and degassed; either by reducing the pressure until the solvent began to boil and backfilling with nitrogen 3 times, or by bubbling nitrogen through the solution for at least 20 minutes.

The (R,R)-N-tosyl-1,2-diamino-1,2-diphenylethane and ruthenium compound were weighed out into a clean dry Schlenk flask. The flask was stoppered with a 'Suba-seal' (RTM). Its contents were evacuated, then purged at room temperature by 3 changes of nitrogen. The mixture was heated at 80° C. for 1 hour. The propan-2-ol solvent was then removed in vacuo and the catalyst dried in vacuo at ambient temperature for 2 hours. The residue was dissolved in acetonitrile to form a 2.49 mM solution.

| Transfer Hydrogenation Reactant | Wt/Vol | Mol.Wt | Mol | Mol ratio |
|---|---|---|---|---|
| (R,R)-Ru(p-Cymyl)Cl N-Tosyl-1,2-diamino-1,2-diphenylethane | 2 ml of 2.49 mM soln | | 4.98 μmol | 200 |
| N-methyl-1-phenyl-6,7-dimethoxy-3,4-dihydroisoquinolinium iodide | 0.409 g | 409 | 1 mmol | 1 |
| Acetonitrile | 2 ml | — | — | — |
| Et$_3$N/HCO$_2$H [2:5] | 0.5 ml | — | 6 mmol of HCO$_2$H | 6 of HCO$_2$H |

The N-methyl-1-phenyl-6,7-dimethoxy-3,4-dihydroisoquinolinium iodide was dissolved in acetonitrile (2 ml) then degassed. To this was added a solution of the catalyst in acetonitrile (2 ml). The reaction was started by the addition of a triethylamine/formic acid mixture [2:5]. The reaction was sampled at regular intervals. The samples (0.25 ml) were each immediately worked up by the addition of dichloromethane (4 ml) and washing the organic phase with saturated sodium hydrogen carbonate solution (3 ml). Upon drying the organic phase by contacting with solid anhydrous magnesium sulphate and then filtering off the solid, the solvent was removed in vacuo. The samples were analysed by $^1$H NMR.

After 20 hours the reaction was complete (>98% conversion).

EXAMPLE 2

Reduction of N-methyl-1-phenyl-6,7-dimethoxy-3,4-dihydroisoquinolinium iodide

| Catalyst Preparation Reactant | Wt/Vol | Mol.Wt | Mol | Mol ratio |
|---|---|---|---|---|
| [Ru(p-Cymyl)Cl$_2$]$_2$** | 7.6 mg | 612 | 12.4 μmol | 1 |
| (R,R)-N-Tosyl-1,2-diamino-1,2-diphenylethane | 9.1 mg | 366 | 24.9 μmol | 2 |
| Acetonitrile | 10 ml | | | |
| Propan-2-ol | 10 ml | | | |

Notes: **purchased from The Aldrich Chemical Co.

Prior to the reaction, all solvents were degassed, for example: 100 ml of anhydrous propan-2-ol was added by syringe to a sealed clean dry round bottomed flask and degassed; either by reducing the pressure until the solvent began to boil and backfilling with nitrogen 3 times, or by bubbling nitrogen through the solution for at least 20 minutes.

The (R,R)-N-tosyl-1,2-diamino-1,2-diphenylethane and ruthenium compound were weighed out into a clean dry Schlenk flask. The flask was stoppered with a 'Suba-seal' (RTM). Its contents were evacuated, then purged at room temperature by 3 changes of nitrogen. The mixture was heated at 80° C. for 1 hour. The propan-2-ol solvent was then removed in vacuo and the catalyst dried in vacuo at ambient temperature for 2 hours. The residue was dissolved in acetonitrile to form a 2.49 mM solution.

| Transfer Hydrogenation Reactant | Wt/Vol | Mol.Wt | Mol | Mol ratio |
|---|---|---|---|---|
| (R,R)-Ru(p-Cymyl)Cl N-Tosyl-1,2-diamino-1,2-diphenylethane | 3 ml of 2.49 mM soln | | 7.47 μmol | 200 |
| N-methyl-1-phenyl-6,7-dimethoxy-3,4-dihydroisoquinolinium iodide | 0.614 g | 409 | 1.5 mmol | 1 |
| Acetonitrile | 3 ml | — | — | — |
| Et$_3$N/HCO$_2$H [2:5] | 0.75 ml | — | 9 mmol of HCO$_2$H | 6 of HCO$_2$H |

The N-methyl-1-phenyl-6,7-dimethoxy-3,4-dihydroisoquinolinium iodide was dissolved in acetonitrile (3 ml) then degassed. To this was added a solution of the catalyst in acetonitrile (3 ml). The reaction was started by the addition of a triethylamine/formic acid mixture [2:5]. The reaction was sampled at regular intervals. The samples (0.25 ml) were each immediately worked up by the addition of dichloromethane (4 ml) and washing the organic phase with saturated sodium hydrogen carbonate solution (3 ml). Upon drying the organic phase by contacting with solid anhydrous magnesium sulphate and then filtering off the solid, the solvent was removed in vacuo. The samples were analysed by $^1$H NMR.

After 2 days the reaction was complete (>99% conversion) with 69%ee.

EXAMPLES 3 TO 6

General Procedures

Prior to the reaction, all solvents were degassed, for example: 100 mL of anhydrous acetonitrile was added by syringe to a sealed clean dry round bottomed flask and degassed; either by reducing the pressure until the solvent began to boil and backfilling with nitrogen 3 times, or by bubbling nitrogen through the solution for at least 20 minutes.

The triethylamine/formic acid mixture used as the reductant system was prepared as follows. Freshly distilled formic acid (41.5 ml, 50.6 g, 1.1 mol) was added slowly to triethylamine (58.8 ml, 44.82 g, 0.44 mol) with stirring and cooling (ice bath) under a nitrogen atmosphere to afford a mixture consisting of a 5:2 molar ratio of formic acid:triethylamine.

Preparation of Starting Materials

Preparation of N-Methyl-1-phenyl-6,7-dimethoxy-3,4-dihydroisoquinolinium iodide

| Reactant | Wt or Vol | Mol.Wt | mMol | Mol ratio |
|---|---|---|---|---|
| Methyl iodide* | 0.94 ml | 142 | 15 | 1.5 |
| Acetone* | 50 ml | | | |
| 1-Phenyl-6,7-dimethoxy-3,4-dihydroisoquinoline** | 2.67 g | 267 | 10 | 1 |

*Purchased from the Aldrich Chemical Co.
**Purchased from ACROS

To a stirred solution of 1-phenyl-6,7-dimethoxy-3,4-dihydroisoquinoline in acetone was added methyl iodide and the reaction mixture was stirred at room temperature for 16 hours. A pale yellow precipitate was formed. The by-products and unreacted methyl iodide were removed in vacuo to afford the desired compound in 93% yield.

Preparation of N-Methyl-1-methyl-6,7-dimethoxy-3, 4-dihydroisoquinolinium iodide

| Reactant | Wt or Vol | Mol.Wt | mMol | Mol ratio |
|---|---|---|---|---|
| Methyl Iodide* | 0.6 ml | 142 | 10 | 2 |
| Acetone* | 250 ml | | | |
| 1-Methyl-6,7-dimethoxy-3,4-dihydroisoquinoline** | 1.025 g | 205 | 5 | 1 |

*Purchased from the Aldrich Chemical Co.
**Purchased from ACROS

To a stirred solution of 1-methyl-6,7-dimethoxy-3,4-dihydroisoquinoline in acetone was added methyl iodide and the reaction mixture was stirred at room temperature for 16 hours. A bright yellow precipitate formed. The by-products and methyl iodide were removed in vacuo to afford the desired compound in 95% yield.

Preparation of N-Benzyl-1-methyl-6,7-dimethoxy-3, 4-dihydroisoquinolinium bromide

| Reactant | Wt or Vol | Mol.Wt | mMol | Mol ratio |
|---|---|---|---|---|
| Benzyl Bromide* | 1.71 g | 171 | 10 | 2 |
| Acetone* | 10 ml | | | |
| 1-Methyl-6,7-dimethoxy-3,4-dihydroisoquinoline** | 1.00 g | 205 | 4.8 | 1 |

*Purchased from the Aldrich Chemical Co.
**Purchased from ACROS

To a stirred solution of 1-methyl-6,7-dimethoxy-3,4-dihydroisoquinoline in acetone was added benzyl bromide and the reaction mixture was stirred at room temperature for 16 hours. A yellow precipitate formed which was filtered, washed with ice cold acetone and dried in vacuo. The product was further purified by recrystallisation from a hexane/dichloromethane mix and pentane to afford the desired compound in 81% yield.

Preparation of N-benzyl-indoleninium bromide

| Reactant | Wt or Vol | Mol.Wt | mMol | Mol ratio |
|---|---|---|---|---|
| Benzyl Bromide* | 10.52 g | 171 | 62 | 2 |
| Acetone* | 70 ml | | | |
| Indolenine | 5.00 g | 159 | 31 | 1 |

*Purchased from the Aldrich Chemical Co.

To a stirred solution of indolenine in acetone was added benzyl bromide and the reaction mixture was stirred at room temperature for 16 hours. A precipitate formed which was filtered and dried in vacuo. The product was further purified by recrystallisation from a hexane/dichloromethane mix and pentane to afford the desired compound in 10% yield.

Transfer Hydrogenation Reactions

EXAMPLE 3

Transfer Hydrogenation of N-methyl-1-phenyl-6,7-dimethoxy-3,4-dihydroisoquinolinium iodide

| Reactant | Wt or Vol | Mol.Wt | mMol | Mol ratio |
|---|---|---|---|---|
| [Ru(p-Cymyl)Cl$_2$]$_2$* | 2.3 mg | 612 | 0.00375 | 0.5 |
| (R,R)-N-Tosyl-1,2-diamino-1,2-diphenylethane | 2.8 mg | 366 | 0.0075 | 1 |
| Triethylamine/Formic Acid (2/5 Molar ratio) | 0.75 ml | | 9 (wrt formic acid) | 1200 (wrt formic acid) |
| Acetonitrile | 5 ml | | | |
| N-methyl-1-methyl-6,7-dimethoxy-3,4-dihydroisoquinolinium iodide | 0.610 g | 407 | 1.5 | 200 |

*Compound purchased from the Aldrich Chemical Company.
**Compound purchased from the Fisher Scientific.

The (R,R)-N-tosyl-1,2-diamino-1,2-diphenylethane, ruthenium dichloride dimer and N-methyl-1-phenyl-6,7-dimethoxy-3,4-dihydroisoquinolinium iodide were weighed out into a clean dry Schlenk flask. The flask was stoppered with a 'Suba-seal' (RTM), evacuated, then backfilled with nitrogen 3 times. The solids were dissolved in acetonitrile and a nitrogen sparge was applied. The reaction mixture was stirred for 5–10 minutes before the formic acid/triethylamine mixture was added to initiate the reaction. The reaction was sampled at regular intervals. The samples (0.25 ml) were immediately worked up by the addition of dichloromethane (4 ml) and the organic phase washed with saturated sodium hydrogen carbonate solution (4 ml). After drying the organic phase over solid anhydrous magnesium sulphate and then filtering off the solid, the solvent was removed in vacuo to afford a white powder. The samples were analysed by chiral HPLC. After 2 hours the reaction was 87% complete and after 7 hours the reaction was >98% complete forming the desired product in ~60%ee.

EXAMPLE 4

Transfer Hydrogenation of N-Methyl-1-methyl-6,7-dimethoxy-3,4-dihydroisoquinolinium iodide

| Reactant | Wt or Vol | Mol.Wt | mMol | Mol ratio |
|---|---|---|---|---|
| [Ru(p-Cymyl)Cl$_2$]$_2$* | 1.6 mg | 612 | 0.0025 | 0.5 |
| (R,R)-N-Tosyl-1,2-diamino-1,2-diphenylethane | 1.8 mg | 366 | 0.005 | 1 |
| iso-Propanol** | 19 ml | | | excess |
| Sodium iso-propoxide, in i-PrOH | 1.5 ml 0.1M | | 0.15 | 3 |
| N-methyl-1-methyl-6,7-dimethoxy-3,4-dihydroisoquinolinium iodide | 0.347 g | 347 | 1 | 200 |

*Compound purchased from the Aldrich Chemical Company.
**Compound purchased from the Fisher Scientific.

The (R,R)-N-tosyl-1,2-diamino-1,2-diphenylethane and ruthenium dichloride dimer were weighed out into a clean dry Schlenk flask. The flask was stoppered with a 'Suba-seal' (RTM), evacuated, then backfilled with nitrogen 3 times. The solids were dissolved in iso-propanol. The reaction mixture was stirred overnight before N-methyl-1- methyl-6,7-dimethoxy-3,4-dihydroisoquinolinium iodide was added. Once the solids had dissolved the sodium iso-propoxide was added in one aliquot to start the reaction. The reaction mixture was heated to 40° C. and stirred.

The reaction was sampled at regular intervals. The samples (0.25 ml) were immediately worked up. The solvent was removed in vacuo and the residue taken up in dichloromethane (4 ml). The organic phase was washed with saturated sodium hydrogen carbonate solution (4ml). After drying the organic phase over solid anhydrous magnesium sulphate and then filtering off the solid, the solvent was removed in vacuo to afford an off-white powder. The samples were analysed by $^1$H NMR and the ee determined by chiral HPLC.

After 48 hours the reaction was 72% complete forming the desired product with 63%ee.

EXAMPLE 5

Transfer Hydrogenation of N-Benzyl-1-methyl-6,7-dimethoxy-3,4-dihydroisoquinolinium bromide

| Reactant | Wt or Vol | Mol.Wt | mMol | Mol ratio |
|---|---|---|---|---|
| [Ru(p-Cymyl)Cl$_2$]$_2$* | 1.6 mg | 612 | 0.0025 | 0.5 |
| (R,R)-N-Tosyl-1,2-diamino-1,2-diphenylethane | 1.8 mg | 366 | 0.005 | 1 |
| iso-Propanol** | 19 ml | | | excess |
| Sodium iso-propoxide, in i-PrOH | 1.5 ml 0.1M | | 0.15 | 3 |
| N-benzyl-1-methyl-6,7-dimethoxy-3,4-dihydroisoquinolinium bromide | 0.376 g | 376 | 1 | 200 |

*Compound purchased from the Aldrich Chemical Company.
**Compound purchased from the Fisher Scientific.

The (R,R)-N-tosyl-1,2-diamino-1,2-diphenylethane and ruthenium dichloride dimer were weighed out into a clean dry Schlenk flask. The flask was stoppered with a 'Suba-seal' (RTM), evacuated, then backfilled with nitrogen 3 times. The solids were dissolved in iso-propanol. The reaction mixture was stirred overnight before N-benzyl-1-methyl-6,7-dimethoxy-3,4-dihydroisoquinolinium bromide was added. Once the solids had dissolved the sodium iso-propoxide was added in one aliquot to start the reaction. The reaction mixture was heated to 40° C. and stirred.

The reaction was sampled at regular intervals. The samples (0.25 ml) were immediately worked up. The solvent was removed in vacuo and the residue taken up in dichloromethane (4 ml). The organic phase was washed with saturated sodium hydrogen carbonate solution (4 ml). After drying the organic phase over solid anhydrous magnesium sulphate and then filtering off the solid, the solvent was removed in vacuo to afford an off-white powder. The samples were analysed by $^1$H NMR and the ee determined by chiral HPLC.

After 48 hours the reaction was 73% complete forming the desired product with 69%ee.

EXAMPLE 6

Transfer Hydrogenation of N-Benzyl-indoleninium bromide

| Reactant | Wt or Vol | Mol.Wt | mMol | Mol ratio |
|---|---|---|---|---|
| [Ru(p-Cymyl)Cl$_2$]$_2$* | 1.53 mg | 612 | 0.0025 | 0.5 |
| (R,R)-N-Tosyl-1,2-diamino-1,2-diphenylethane | 1.8 mg | 366 | 0.005 | 1 |
| Triethylamine/Formic Acid (1/50 Molar ratio) | 1 ml | | 29 (wrt formic acid) | 5800 (wrt formic acid) |
| Acetonitrile** | 3 ml | | | |
| N-Benzyl-indoleninium bromide | 1.34 g | 159 | 1 | 200 |

*Compound purchased from the Aldrich Chemical Company.
**Compound purchased from the Fisher Scientific.

The (R,R)-N-tosyl-1,2-diamino-1,2-diphenylethane, ruthenium dichloride dimer and the N-benzyl-indoleninium bromide were weighed out into a clean dry Schlenk flask. The flask was stoppered with a 'Suba-seal' (RTM), evacuated, then backfilled with nitrogen 3 times. The solids were dissolved in acetonitrile. The reaction mixture was stirred for 5–10 minutes before the formic acid/triethylamine mixture was added to initiate the reaction.

The reaction was sampled at regular intervals. The samples (0.25 ml) were immediately worked up by the addition of dichloromethane (4 ml) and the organic phase washed with saturated sodium hydrogen carbonate solution (4 ml). After drying the organic phase over solid anhydrous magnesium sulphate and then filtering off the solid, the solvent was removed in vacuo to afford a white powder. The samples were analysed by $^1$H NMR.

After 22 hours the reduction was >98% complete.

We claim:

1. A process for the transfer hydrogenation of a compound of formula (1)

(1)

wherein:

X represents $(NR^3R^4)^+Q^-$, $N^+R^5$—$O^-$, $(NR^6OR^7)^+Q^-$, $(NR^8NR^9R^{10})^+Q^-$, $(NR^8NR^9C(=NR^{11})R^{12})^+Q^-$, $(NR^8NR^9SO_2R^{13})^+Q^-$, or $(NR^8NR^9COR^{14})^+Q^-$;

$Q^-$ represents a monovalent anion;

$R^1$, $R^2$, $R^3$, $R^4$, $R^5$, $R^6$, $R^7$, $R^8$, $R^9$, $R^{10}$, and $R^{11}$ each independently represents a hydrogen atom, an optionally substituted hydrocarbyl, a perhalogenated hydrocarbyl or an optionally substituted heterocyclyl group, one or more of $R^1$ & $R^2$, $R^1$ & $R^3$, $R^2$ & $R^4$, $R^3$ & $R^4$, $R^1$ & $R^5$, $R^1$ & $R^6$, $R^2$ & $R^7$, $R^1$ & $R^8$, $R^1$ & $R^9$, $R^6$ & $R^7$, $R^8$ & $R^9$ and $R^9$ & $R^{10}$ optionally being linked in such a way as to form an optionally substituted ring(s); and $R^{12}$, $R^{13}$ and $R^{14}$ each independently represents an optionally substituted hydrocarbyl, a perhalogenated hydrocarbyl or an optionally substituted heterocyclyl group;

said process comprising reacting the compound of formula (1) with a hydrogen donor in the presence of a catalyst, characterised in that the catalyst has the general formula:

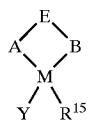

wherein:
R$^{15}$ represents a neutral optionally substituted hydrocarbyl or perhalogenated hydrocarbyl ligand;

A represents —NR$^{16}$—, —NR$^{17}$—, —NHR$^{16}$, —NR$^{16}$R$^{17}$ or —NR$^{17}$R$^{18}$ where R$^{16}$ is H, C(O)R$^{18}$, SO$_2$R$^{18}$, C(O)NR$^{18}$R$^{22}$, C(S)NR$^{18}$R$^{22}$, C(=NR$^{22}$)SR$^{23}$ or C(=NR$^{22}$)OR$^{23}$, R$^{17}$ and R$^{18}$ each independently represents an optionally substituted hydrocarbyl, perhalogenated hydrocarbyl or an optionally substituted heterocyclyl group, and R$^{22}$ and R$^{23}$ are each independently hydrogen or a group as defined for R$^{18}$;

B represents —O—, —OH, OR$^{19}$, —S—, —SH, SR$^{19}$, —NR$^{19}$—, —NR$^{20}$—, —NHR$^{20}$, —NR$^{19}$R$^{20}$, —NR$^{19}$R$^{21}$, —PR$^{19}$— or —PR$^{19}$R$^{21}$ where R$^{20}$ is H, C(O)R$^{21}$, SO$_2$R$^{21}$, C(O)NR$^{21}$R$^{24}$, C(S)NR$^{21}$R$^{24}$, C(=NR$^{24}$)SR$^{25}$ or C(=NR$^{24}$)OR$^{25}$, R$^{19}$ and R$^{21}$ each independently represents an optionally substituted hydrocarbyl, perhalogenated hydrocarbyl or an optionally substituted heterocyclyl group, and R$^{24}$ and R$^{25}$ are each independently hydrogen or a group as defined for R$^{21}$;

E represents a linking group wherein A and B are linked through 2, 3 or 4 optionally substituted atoms;

M represents a group VIII transition metal; and

Y represents an anionic group, a basic ligand or a vacant site;

provided that when Y is not a vacant site that at least one of A or B carries a hydrogen atom.

2. A process according to claim 1, wherein M is ruthenium, rhodium or imidium.

3. A process according to claim 1 or claim 2, wherein R$^{15}$ is an optionally substituted aryl or an optionally substituted alkene.

4. A process according to claim 1 or claim 2 in which A is —NR$^{16}$—, —NR$^{17}$—, —NHR$^{18}$, —NR$^{16}$R$^{17}$R$^{18}$, and B is —O—, —OH, OR$^{18}$, —NR$^{19}$—, —NR$^{20}$—, —NHR$^{20}$, —NR$^{19}$R$^{20}$ or —NR$^{18}$R$^{21}$.

5. A process according to claim 4, wherein one of A or B has an R$^{16}$ or R$^{20}$ group and that said R$^{16}$ or R$^{20}$ is C(O)R$^{21}$ or SO$_2$R$^{21}$.

6. A process according to claim 4 in which A-E-B is, or is derived from, one of the following:

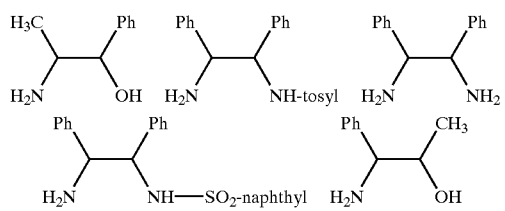

-continued

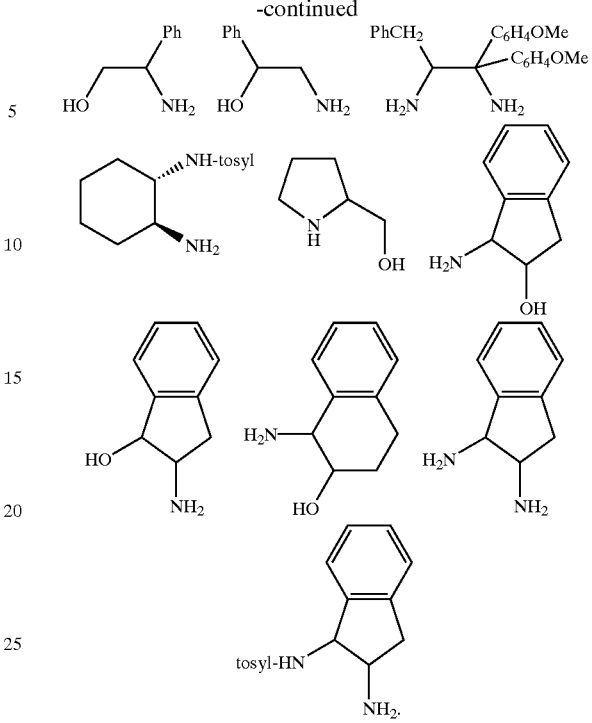

7. A process according to claim 1 or claim 2, wherein the compound of formula (1) is prochiral and the catalyst is chiral, an enantiomerically and/or diastereomerically purified form of the catalyst being employed, whereby the compound of formula (1) is asymmetrically hydrogenated.

8. A process according to claim 7, in which A-E-B comprises at least one stereospecific centre.

9. A process according to claim 1 or claim 2, in which the hydrogen donor is selected from hydrogen, primary and secondary alcohols, primary and secondary amines, carboxylic acids and their esters and amine salts, readily dehydrogenatable hydrocarbons, clean reducing agents, and any combination thereof.

10. A process according to claim 9 in which the hydrogen donor is a mixture of triethylamine and formic acid.

11. A process according to claim 1 or claim 2, in which the products from dehydrogenation of the hydrogen donor are removed by inert gas sparging or vacuum distillation.

12. A process according to claim 1 or claim 2, in which the process is carried out in presence of a base having a pK$_a$ of at least 8.0.

13. A process according to claim 5 wherein R$^{18}$ or R$^{20}$ is a toluenesulphonyl, methanesulphonyl, trifluoromethanesulphonyl or acetyl group.

14. A process according to claim 4 when B is —O—, —OH or OR$^{18}$, E is a linking group wherein A and B are lined through 2 or 3 carbon atoms, and when B is —NR$^{19}$—, —NR$^{20}$—, NHR$^{20}$, —NR$^{19}$R$^{20}$, E is a linking group wherein A and B are linked through 2 carbon atoms.

15. A process according to claim 1 or claim 2, wherein R$^{15}$ is an optionally substituted aryl or an optionally substituted alkene; A is —NR$^{16}$—, —NR$^{17}$—, —NHR$^{18}$, —NR$^{16}$R$^{17}$ or —NR$^{17}$R$^{18}$; and B is —O—, —OH, OR$^{18}$, —NR$^{19}$, —NR$^{20}$—, —NHR$^{20}$, —NR$^{19}$R$^{20}$ or —NR$^{19}$R$^{21}$.

16. A process according to claim 15, in which the hydrogen donor is a mixture of triethylamine and formic acid.

17. A process according to claim 16, wherein one of A or B has an R$^{16}$ or R$^{20}$ group and that said R$^{16}$ or R$^{20}$ is C(O)R$^{21}$ or SO$_2$R$^{21}$.

18. A process according to claim 17, in which A-E-B comprises at least one stereospecific center.

19. A process according to claim 2, wherein X represents $(NR^3R^4)^+Q$ and, $R^1$, $R^2$, $R^3$ and $R^4$ each independently represents an optionally substituted hydrocarbyl, a perhalogenated hydrocarbyl or an optionally substituted heterocyclyl group, or one or more of $R^1$ & $R^2$, $R^1$ & $R^3$, $R^2$ & $R^4$ and $R^3$ & $R^4$ optionally being linked in such a way as to form an optionally substituted ring(s).

20. A process according to claim 13, wherein a compound of formula (1) is transfer hydrogenated in the presence of a catalyst in which A is —$NR^{16}$—, —$NR^{17}$—, —$NHR^{16}$, —$NR^{16}R^{17}$ or —$NR^{17}R^{18}$; and B is —$NR^{19}$—, —$NR^{20}$—, —$NHR^{20}$, —$NR^{19}R^{20}$ or —$NR^{19}R^{21}$ and wherein one of A or B has an $R^{16}$ or $R^{20}$ group and that said $R^{16}$ or $R^{20}$ group is toluenesulphonyl.

* * * * *